(12) United States Patent
Zapf et al.

(10) Patent No.: US 7,094,999 B2
(45) Date of Patent: Aug. 22, 2006

(54) APPARATUS FOR STERILIZING OBJECTS

(75) Inventors: Manfred Zapf, Hochstiftstr.6, D-87561 Oberstdorf (DE); Detlef Schiller, Fürth (DE)

(73) Assignee: Manfred Zapf, Oberstdorf (DE)

( * ) Notice: Subject to any disclaimer, the term of this patent is extended or adjusted under 35 U.S.C. 154(b) by 0 days.

(21) Appl. No.: 10/963,018

(22) Filed: Oct. 12, 2004

(65) Prior Publication Data

US 2005/0127069 A1    Jun. 16, 2005

(30) Foreign Application Priority Data

Dec. 9, 2003    (DE)    ............... 203 15 802 U

(51) Int. Cl.
*H05B 6/64*    (2006.01)

(52) U.S. Cl. ...................... 219/756; 219/757

(58) Field of Classification Search ............... 219/756, 219/757, 741, 400, 711, 719, 720, 700, 679, 219/709, 704–705, 696, 746, 748, 730, 759, 219/736; 126/21 A, 198; 435/7.1; 422/21; 264/402, 405

See application file for complete search history.

(56) References Cited

U.S. PATENT DOCUMENTS

| | | | | |
|---|---|---|---|---|
| 3,480,753 A | * | 11/1969 | Pharr, Jr. et al. | 219/741 |
| 4,851,632 A | * | 7/1989 | Kaliski | 219/730 |
| 5,039,495 A | * | 8/1991 | Kutner et al. | 422/299 |
| 5,245,149 A | * | 9/1993 | Pinna et al. | 219/700 |
| 5,858,303 A | * | 1/1999 | Schiffmann et al. | 422/21 |
| 6,441,354 B1 | * | 8/2002 | Seghatol et al. | 219/679 |

* cited by examiner

*Primary Examiner*—Quang Van
(74) *Attorney, Agent, or Firm*—Collard & Roe, P.C.

(57) ABSTRACT

An apparatus for sterilizing objects has a sterilization chamber and a microwave source for applying microwave radiation to objects inside the sterilization chamber.

12 Claims, 2 Drawing Sheets

APPARATUS FOR STERILIZING OBJECTS

BACKGROUND OF THE INVENTION

1. Field of the Invention

The invention relates to an apparatus for sterilizing objects, particularly mattresses, blankets, wooden furniture, clothing, etc.

2. The Prior Art

There have been many different apparatuses for sterilizing objects, but they all have the disadvantage that complicated technical facilities are required to operate them. Use of such a sterilizer at home is not possible in the vast majority of cases, because of the high costs incurred.

SUMMARY OF THE INVENTION

It is therefore an object of the invention to provide an apparatus for sterilizing objects that is easy and inexpensive to use.

This object is achieved by providing a sterilizing apparatus having a microwave source assigned to the sterilization chamber.

This minimizes the costs incurred. Mites, fleas, bacteria, woodworms or similar organisms can be killed simply by the microwave radiation.

In a preferred embodiment, the microwave source is in the form of a magnetron and is provided with a shield. The microwave radiation is directed towards the sterilization chamber as a result.

In another embodiment, a device is provided that can interrupt the microwaves. This means that the microwave radiation can be applied to the sterilization chamber in a pulsed manner. It is advantageous if at least one metallized propeller is provided for the periodic interruption of the microwave radiation. The microwave radiation is simple to interrupt in this way.

It is advantageous if the walls of the sterilization chamber are designed to that they reflect microwave radiation. This prevents microwaves from leaving the sterilization chamber. An additional effect is that the whole of the sterilization chamber is reached by the microwaves.

It is also advantageous if the walls fo the sterilization chamber consist of an at least partially metallized plastic film and/or a metal foil. This means that the sterilization chamber can be designed to be flexible, as a result of which it can be folded or rolled together when it is not in use.

In another embodiment, the walls of the sterilization chamber consist of a grid screen that reflects microwaves. A grid screen makes sure that there is adequate reflection and shielding, while material can be saved at the same time. The sterilizer can thus be used even more flexibly.

In another embodiment, the walls of the chamber consist of any rigid or flexible material that is metallized or provided with a second layer that reflects microwave radiation. Permanent sterilization chambers, for stationary applications, can be built with this material too.

In another embodiment, a screen is provided between the microwave source and the sterilization chamber to distribute the microwave radiation more effectively.

Depending on its mesh width and geometric shape, such a screen makes sure that the radiation emitted by the microwave source is distributed as consistently as possible in the sterilization chamber by means of interference and superposition.

It is also advantageous if two or more microwave sources are provided, which can be located on one side of the sterilization chamber and/or on different sides of the sterilization chamber. The capacity of the sterilizer can be set almost at will as a result. It is also possible to guarantee good coverage, by arranging microwave sources on opposite sides of the sterilization chamber. It is also advantageous if a device is provided which allows one or more microwave sources to be moved automatically or manually, particularly along the sides of the sterilization chamber. This means that one or more microwave sources can be moved over the object that is to be sterilized, as a result of which very large objects such as mattresses can be sterilized too.

Preferably, a door, flap or something similar is provided to open and close the sterilization chamber. Objects can be brought into and removed again from the sterilization chamber simply as a result.

In another advantageous embodiment, a safety device is provided which prevents accidental emission of microwave radiation, particularly when the sterilization chamber is not closed. Unintentional injury to people is effectively prevented as a result.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
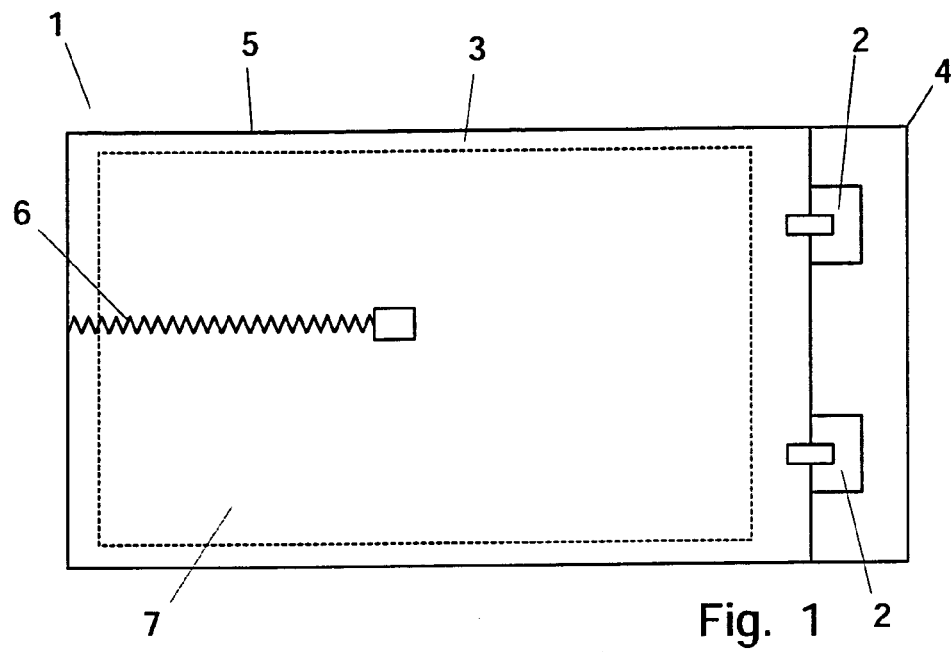
FIG. 1 shows a diagram of a sterilizer in accordance with the invention.
Figure 2:
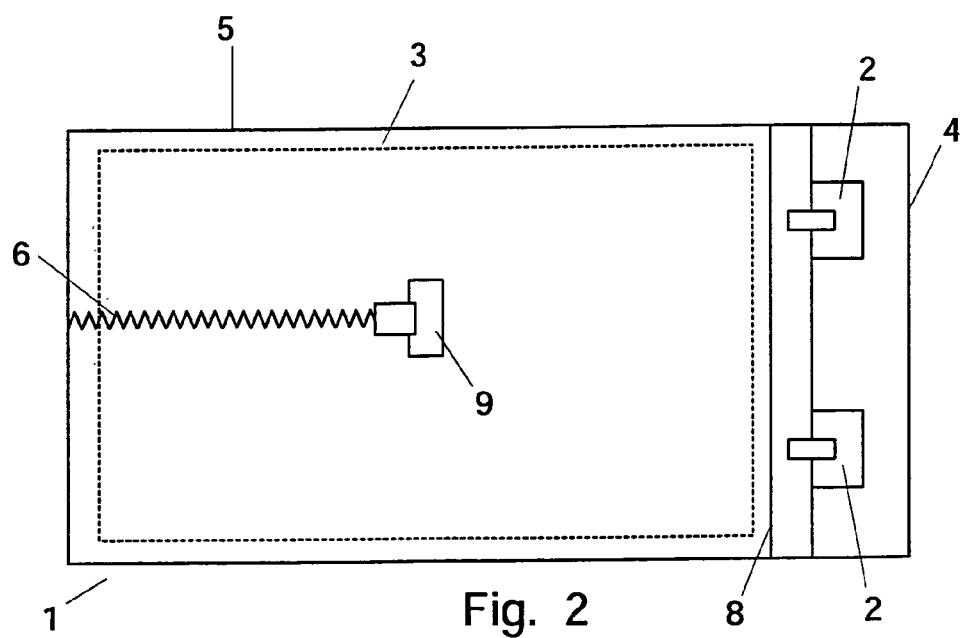
FIG. 2 shows a diagram of another sterilizer in accordance with the invention.

Referring now in detail to the drawings, FIG. 1 shows a sterilizer for killing mites, fleas, lice, bacteria, woodworms, or similar organisms with a microwave source 2 and a sterilization chamber 3. Microwave source 2 is surrounded by a shield 4, which makes sure that the microwaves can only escape in the direction of sterilization chamber 3. Sterilization chamber 3 is located right next to the shield 4 of the microwave source 2 and is open towards it.

Sterilization chamber 3 is surrounded in all other directions by a metallized plastic film 5, which reflects the microwave radiation and thus stops it, leaving the sterilization chamber 3. Sterilization chamber 3 can be opened with a zip 6 and can then be loaded.

Sterilizer 1 is suitable for sterilizing mattresses, blankets, wooden furniture or similar objects. After sterilization chamber 3 has been loaded with the objects that are to be sterilized 7, zip 6 is closed again.

Microwave source 2 is activated for a short time for sterilization purposes. The microwave radiation makes sure that the pests are killed by heating them.

After the microwave source2 has been switched off, the objects that have been sterilized 7 can be taken out of sterilization chamber 3. A standard magnetron similar to the type used in microwave ovens can be used as microwave source 2.

A screen 8, which guarantees consistent distribution of microwave radiation throughout the sterilization chamber 3 by means of refraction, interference and superposition, is located between microwave source 2 and sterilization chamber 3. The mesh width and geometry of screen 8 are adapted to the wavelength of the microwaves and the design of sterilization chamber 3. Screen 8 can be produced from a metal or metallized material like plastic.

The walls of sterilization chamber 3 can be also be produced from a metal foil, a conductive screen of such rigid materials as metal, plastic or wooden boards. Materials that let microwaves through need to be provided with a shield made of metal foil, a metallized material, a screen or something similar.

A door or something similar to it can also be provided to open the sterilization chamber 3 instead of zip 6. It is also conceivable that zip 6 of a door or something similar to it has a safety device 9 which switches off microwave source 2 if and when the sterilization chamber 3 is opened while sterilizer 1 is in operation. If sterilizer 3 is designed to be flexible, it can be rolled up when not in use, so it takes up only a minimum of space.

Several microwave sources 2 can be provided along the sterilization chamber too, which guarantee particularly good coverage of sterilization chamber 3 when they are located opposite each other. Microwave source 2 can be moved across the sterilization chamber and/or over objects that are to be sterilized 7, possibly with its shield 4, and thus passes over the whole of the objects that are to be sterilized 7 during the time it is switched on.

Figure 3:
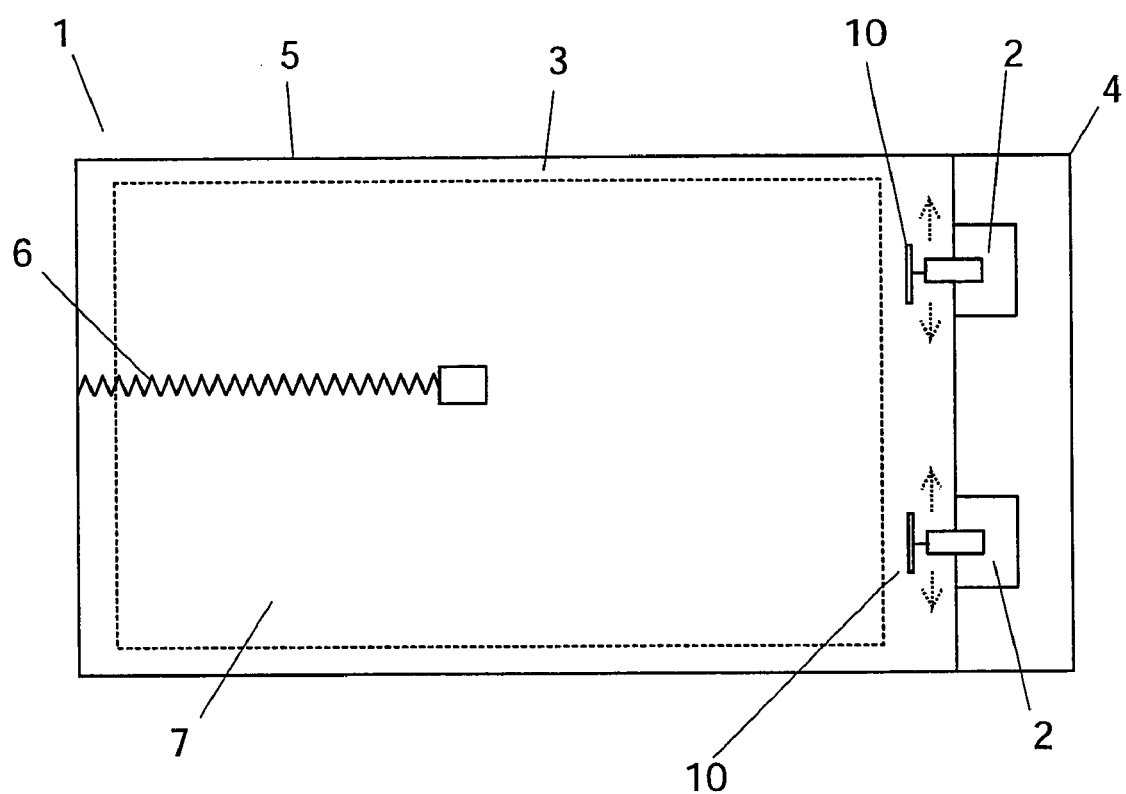
FIG. 3 shows a diagram of an additional sterilizer in accordance with the invention.

FIG. 3 shows a diagram of another embodiment of the sterilizer according to the invention. Here, metallized propellers 10 are installed to periodically interrupt the microwaves, so that the radiation can be applied in a pulsed manner. The microwave sources are movable along the sides of chamber 3, along the arrows shown.

Accordingly, while only a few embodiments of the present invention have been shown and described, it is obvious that many changes and modifications may be made thereunto without departing from the spirit and scope of the invention.

What is claimed is:

1. Apparatus for sterilizing objects comprising a flexible sterilization chamber, a microwave source for applying microwaves to objects inside the sterilization chamber and a safety device for preventing accidental emission of microwave radiation when the sterilization chamber is not closed, wherein the chamber is adapted to be folded or rolled up when not in use.

2. The apparatus according to claim 1, wherein the microwave source is a magnetron provided with a shield.

3. The apparatus according to claim 1, further comprising a device that interrupts the microwaves.

4. The apparatus according to claim 3, wherein the device comprises at least one metallized propeller for periodic interruption of the microwaves.

5. The apparatus according to claim 1, wherein the, walls of the sterilization chamber are designed to reflect microwave radiation.

6. The apparatus according to claim 5, wherein the walls of the sterilization chamber consist of an at least partially metallized plastic film and/or a metal foil.

7. The apparatus according to claim 5, wherein the walls of the sterilization chamber consist of a grid screen that reflects microwaves.

8. The apparatus according to claim 5, wherein the walls of the sterilization chamber consist essentially of any rigid or flexible material that is metallized or provided with a second layer that reflects microwave radiation.

9. The apparatus according to claim 1, further comprising a screen between the microwave source and the sterilization chamber to distribute the microwave radiation more effectively.

10. The apparatus according to claim 1 wherein two or more microwave sources are provided, which can be located on the same or different sides of the sterilization chamber.

11. The apparatus according to claim 1, further comprising a device which allows one or more microwave sources to be moved automatically or manually, particularly along the sides of the sterilization chamber.

12. The apparatus according to claim 1, further comprising a door or flap to open and close the sterilization chamber.

* * * * *